United States Patent [19]

Harvey et al.

[11] Patent Number: 5,431,915
[45] Date of Patent: Jul. 11, 1995

[54] FROZEN ORAL MEDICATION DELIVERY SYSTEM AND METHOD

[76] Inventors: Bryce M. Harvey, 1049 Merrywood Dr., Pike Rd., Ala. 36064; Philip M. Knight, 1820 Alderpoint Dr., Montgomery, Ala. 36106

[21] Appl. No.: 169,060

[22] Filed: Dec. 20, 1993

[51] Int. Cl.[6] .............................................. A61K 47/00
[52] U.S. Cl. ................................... 424/439; 426/100; 426/101; 426/104; 426/111
[58] Field of Search ................ 424/439; 426/100, 101, 426/104, 111

[56] References Cited

U.S. PATENT DOCUMENTS

| | | | |
|---|---|---|---|
| 4,238,475 | 12/1980 | Witzel et al. | 424/48 |
| 4,478,822 | 10/1984 | Haslam et al. | 424/94.6 |
| 4,725,440 | 2/1988 | Ridgway et al. | 4214/465 |
| 4,999,185 | 3/1991 | Takemore et al. | 424/58 |
| 5,132,114 | 7/1992 | Stanley et al. | 424/440 |
| 5,296,236 | 3/1994 | Santus | 424/490 |

*Primary Examiner*—D. Gabrielle Phelan
*Attorney, Agent, or Firm*—Sixbey, Friedman, Leedom & Ferguson

[57] ABSTRACT

An oral medication delivery system and method for pharmaceutically active agents having local and/or systemic effect is provided. The system provides three embodiments of containers in which medication is stably stored, either in liquid suspension or in dry powder form with a delivery liquid, until dispensed for use by a patient. The medication is mixed as required and frozen in the storage container until hard, when it is administered to the patient in the form of a frozen popsicle. One embodiment of the system includes a flexible plastic container which contains the pharmaceutically active agent mixed with a delivery liquid. In other embodiments the medication in powder form and a delivery liquid are stored in a chambered container separated by a rupturable membrane which is ruptured to mix the container contents prior to freezing. The oral medication delivery system of the present invention is particularly well suited for delivering Nystatin to oral candidiasis lesions, particularly to the very young, the elderly and those unable to take medications by traditional administration methods.

19 Claims, 2 Drawing Sheets

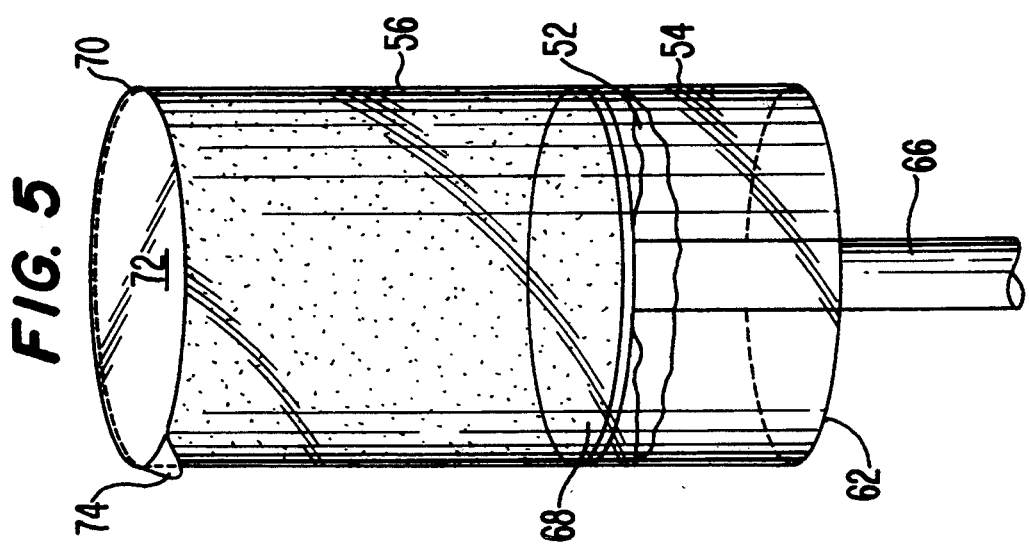
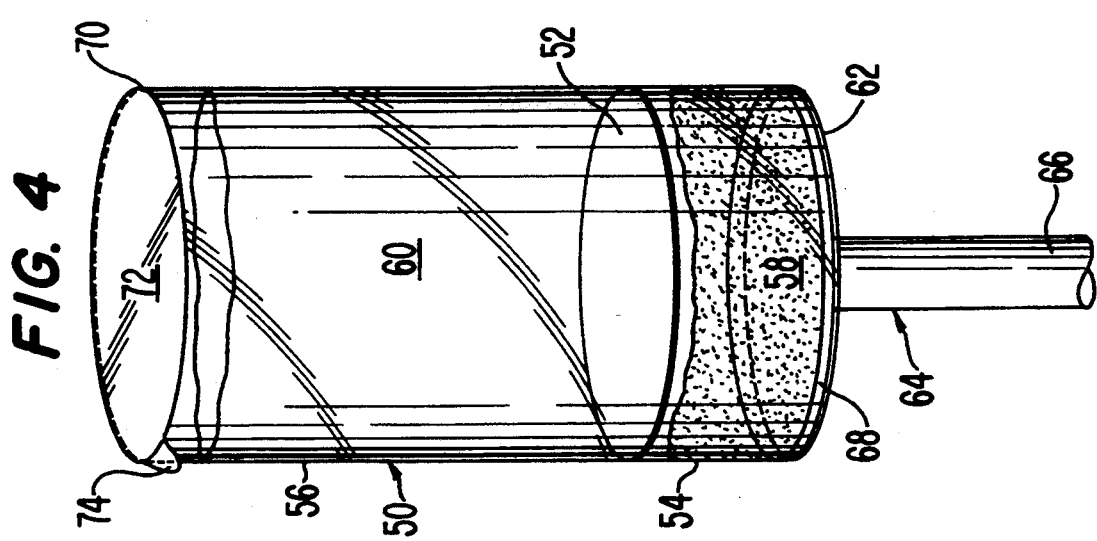
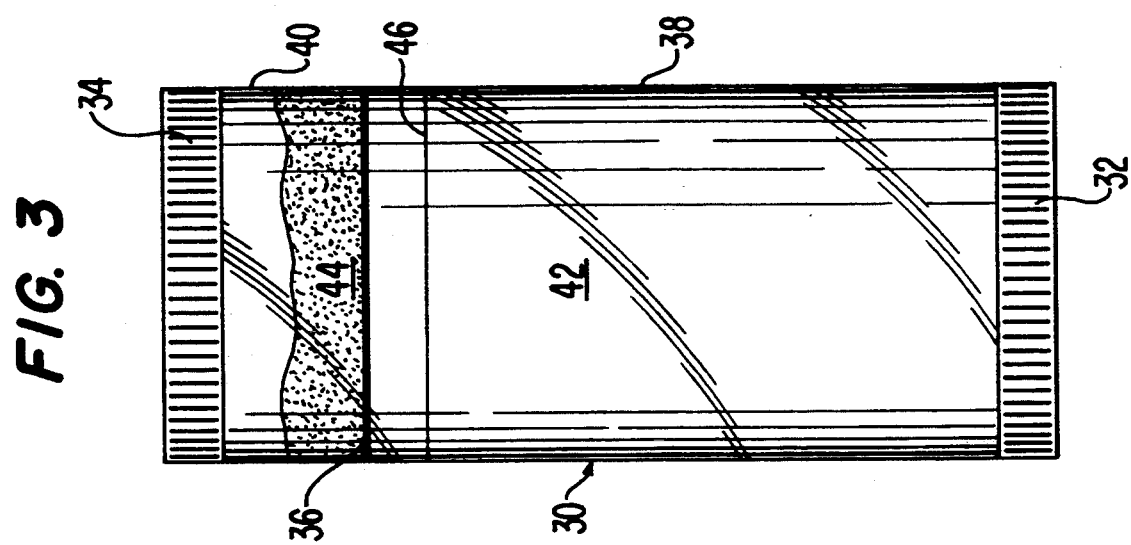

FROZEN ORAL MEDICATION DELIVERY SYSTEM AND METHOD

TECHNICAL FIELD

The present invention is directed generally to a medication delivery system and specifically to an oral medication delivery system and method.

BACKGROUND OF THE INVENTION

Many persons who are ill find it difficult to take medications that are recommended for oral administration. These include both oral medications intended to be effective locally and systemic medications taken by the oral route. The very young and the elderly, in particular, often experience difficulties swallowing orally administered systemic medications. In addition, it is also often very difficult for persons in these groups to retain pastilles, troches or lozenges in their mouths long enough for all of the medication to dissolve and produce the desired local effect.

Patients whose general condition has been weakened by a debilitating disease, radiation therapy, chemotherapy or other condition may require the administration of oral medication to treat the fungus or other infections which often accompany such conditions. One extremely common oral infection encountered in such patients is candidiasis, also known as thrush. This disease, which produces very painful lesions in the oral mucosa, can be quite virulent and even fatal, especially in the very young and elderly. The severe pain associated with oral candidiasis usually limits such patients to the ingestion of only liquids, since solid foods and medications can produce intolerable pain. The currently available forms of medication for this condition are often not well tolerated.

The prior art has suggested various approaches to the administration of oral medication as well as to the oral administration of medication producing systemic effects that are intended to facilitate the administration of such medication. For example, U.S. Pat. No. 4,725,440 to Ridgway et at. discloses an anti-fungal pastille with a soft and smooth texture intended to avoid irritation of the oral mucosa. This pastille is intended to dissolve slowly to deliver the anti-fungal agent, which is preferably Nystatin. Although this is an effective means for maintaining an effective level of medication for the treatment of oral infections, such as thrush, the pastille form of medication is not well tolerated by all patients. Very young children, in particular, often tend to spit the pastille out of the mouth before it has completely dissolved. Some elderly patients also may not be able to retain the pastille for sufficient time to be of optimum therapeutic value. Patients often feel the pastille exacerbates the dry condition of the mouth called "cotton mouth" by patients suffering from oral candidiasis.

U.S. Pat. No. 5,132,114 to Stanley et al. discloses a method for the transmucosal delivery of medication which can have local and/or systemic effect. The therapeutic agent is incorporated into a "candy" matrix in powder form and compressed to form a "lollipop" which includes a suitable holder. This medication delivery system is ideally suited for many patient populations. However, the patient must be strong enough to be able to hold the lollipop in his or her mouth to suck on it. The very young, the elderly and those whose condition has weakened them so that a lollipop cannot be held for a sustained period of time may not be able to use this medication delivery system effectively.

U.S. Pat. No. 4,238,475 to Witzel et al. discloses a chewing gum formulation that releases a small continuous dose of a medication, such as Nystatin, or an orally beneficial material into the mouth. This means of delivering medication to the mouth and oral mucosa can be very effective. However, persons with dentures or bridge work, persons with orthodontic appliances and very young children are unable to chew gum, which limits the use of this medication delivery system to that segment of the population capable of chewing gum comfortably.

U.S. Pat. No. 4,999,185 to Takemori et al. discloses a composition which inhibits sordes formation for application to the oral cavity that may be incorporated into candy, gum, cookies, chocolate milk or ice cream and formulated as a tablet, toothpaste or mouthwash. This composition, which is extracted from cacao husk, bears sufficient resemblance to chocolate to mix readily with food products. It is not suggested that other medicaments or compositions which are unpleasant to the taste could be incorporated into food products to simplify their administration to certain patient populations.

U.S. Pat. No. 4,478,822 to Haslam et al. discloses a drug delivery system which can be used to deliver drugs to, inter alia, the oral cavity. This drug delivery system uses an aqueous vehicle that includes a polymer which causes the aqueous system to form a gel at temperatures encountered in body cavities. While this drug delivery system is probably very effective for delivering medication to many body cavities, it is not likely to be the most effective method of delivering medication to the oral cavities of children.

A need exists, therefore, for a system and method for delivering oral and systemic medication to the oral cavity that (1) may be used effectively by such populations as the very young and the elderly, and (2) not only delivers the medication but provides palliative relief for the soreness and dry condition by the mouth which accompanies many disease states.

SUMMARY OF THE INVENTION

It is a primary object of the present invention, therefore, to provide a system and method for effectively delivering medication to the oral cavity in patient populations such as the very young and the elderly who are unable to tolerate available medication delivery systems and methods.

It is another object of the present invention to provide an oral medication delivery system that includes a freezable delivery liquid containing a pharmaceutically active agent that is frozen for administration in a frozen state.

It is a further object of the present invention to provide an oral medication delivery system for medications that are unstable in liquid suspension, whereby the medication and a flavored liquid may be stored in a storage stable state prior to dispensing and then may be subsequently mixed and frozen for administration in a frozen state.

It is yet another object of the present invention to provide a medication delivery system and method for treating oral candidiasis infections.

It is yet a further object of the present invention to provide an oral medication administration system and method which is readily accepted by children.

It is yet an additional object of the present invention to provide a medication delivery system which is both a vehicle for delivery of a candidiasis medication and by itself treatment for candidiasis.

It is still another object of the present invention to provide an oral medication delivery system and method which effectively administers local oral and systemic medications in a frozen state.

It is still a further object of the present invention to provide, in the treatment of oral candidiasis, an oral medication delivery system and method which provides a significant amount of moisture to the oral cavity.

In accordance with the aforesaid objects, there is provided a method and system for the oral administration of medication that is well tolerated by those unable to tolerate available oral medication delivery and dosage forms. The medication delivery system of the present invention includes a flexible sealed container containing a pharmaceutically effective unit dosage amount of a medication selected to be effective locally or systemically in an aqueous delivery liquid selectively flavored to make the taste of the medication palatable. The medication and liquid-containing container is stored and dispensed and then the container and liquid contents are frozen solid so that the medication is available for administration in a frozen state as a popsicle. In one alternative embodiment, the medication is stored in powder form in one chamber of a freezable flexible container while the flavored aqueous delivery liquid is stored in a another chamber of the container, separated from the first chamber by a rupturable membrane. When the membrane is ruptured, the powdered medication can be mixed with the flavored liquid and the container with the liquid mixture is then frozen until hard so that the medication is administered as a frozen popsicle. A third embodiment provides a rigid container with a rupturable membrane separating two chambers, one containing a delivery liquid and the other containing the medication in powder form. A plunger structure seals the medication-containing chamber and includes a handle that can be used to rupture the membrane and mix the powdered medication with the delivery liquid. After the medication-containing liquid in the container is frozen, a removable seal is removed from the end of the container opposite the plunger, and the frozen popsicle is extruded from the container with the plunger.

The oral administration method comprises providing a unit dosage of a pharmaceutically effective amount of a medication selected to be effective locally or systemically, mixing the medication with an aqueous carder or delivery liquid selectively flavored so that the medication is palatable, adding a selected quantity of the medication-carder liquid mixture to a container formed of a freezable material, sealing the container, shaking the container as required after the medication has been dispensed to distribute the medication evenly throughout the liquid, freezing the medication-containing container until the contents are frozen hard, opening the container and extruding the frozen contents to form a popsicle so that the patient to whom the medication has been dispensed can suck on the frozen contents like a popsicle.

Other objects and advantages will be apparent from the following description, claims and drawings.

BRIEF DESCRIPTION OF THE DRAWINGS

FIG. 3 is a front view of a second embodiment of an oral medication delivery system according to the present invention;

FIG. 4 is a perspective view of a third embodiment of an oral medication delivery system according to the present invention; and FIG. 5 shows the oral medication delivery system of FIG. 4 in which the medication has been mixed with the liquid and the system is ready to be frozen.

DESCRIPTION OF THE PREFERRED EMBODIMENTS

Figure 1:
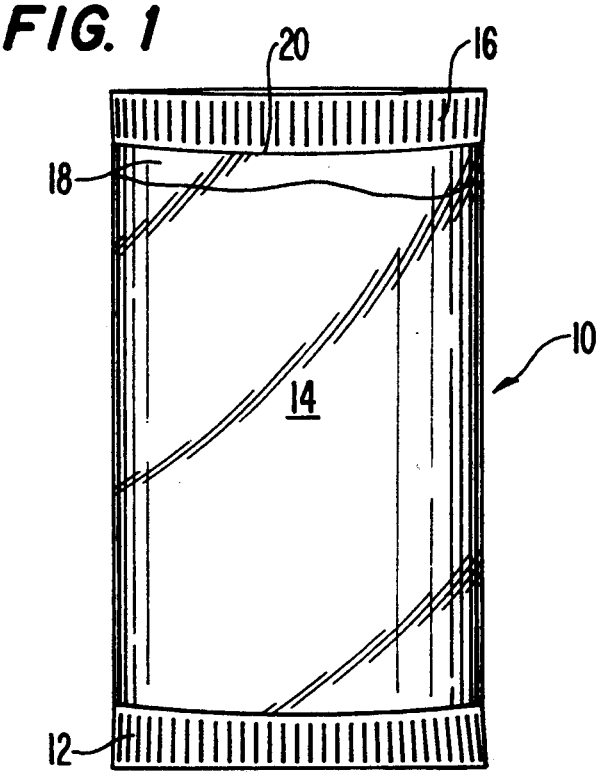
FIG. 1 is a front view of one embodiment of an oral medication delivery system according to the present invention.

Many people experience difficulty with and do not tolerate well the oral administration of medication by currently available methods. There are large numbers of people who, for example, cannot swallow capsules, pills or tablets. Although it is children who have the most problems swallowing oral medication in these forms, many adults also experience varying degrees of difficulty. In addition, the medication-containing pastilles, troches, lollipops and chewing gum of the prior art, while tolerated very well by many people, are unsuitable for the very young and the elderly. Studies have shown, moreover, that approximately 60% of patients do not fully comply with their physician's orders for taking medication. This is a major concern of the medical community.

The present invention provides an oral medication delivery system that is tolerated well by virtually all patients. The oral medication delivery system and method of the present invention can be used both to administer orally medications intended to have a systemic effect and to administer medications intended to be locally effective in the oral cavity. Further, the present medication delivery system is in a form that should significantly increase compliance with medication requirements, particularly in the young and elderly.

There are many disease conditions affecting the oral cavity and surrounding tissues that cause a great deal of pain and discomfort to the patient. Oral candidiasis, which is caused by the fungus *Candida albicans*, is an infection of the mucous membranes of the oral cavity which may spread to other pans of the body. If not treated effectively, a systemic mycosal infection may result. Oral candidiasis is often seen in patients suffering from chronic debilitating diseases such as cancer and diabetes, in patients undergoing antibiotic or hormone therapy, and in patients undergoing chemotherapy or radiation. Many of these patients are very young or elderly. Children with candidiasis that results from chemotherapy for cancer can be particularly difficult to treat because the mouth is extremely sore, inflamed and extremely dry. The available pastille, lollipop and chewing gum which contain pharmacologically effective antifungal agents like Nystatin are not as acceptable to children with this painful condition as the drug delivery system of the present invention.

In one embodiment, the present invention provides a pharmaceutically active agent in a storage stable suspension enclosed in a flexible plastic container that allows the pharmacist or patient to shake the container so that the pharmaceutically active agent is evenly suspended throughout the liquid and then to freeze the suspension until hard. The container is unsealed by removing one end from the plastic container, and the frozen pharmaceutically active agent-containing "popsicle" can be pushed up through the container as it is consumed. The pain of oral candidiasis is relieved by the cold, and the melting popsicle relieves dryness of the mouth. Concurrently, the Nystatin is released into the mouth to contact the candidiasis lesions directly as the patient sucks on the popsicle. Unlike the pastille or lollipop forms of Nystatin which are hard and could further irritate the inflamed mouth tissues, the popsicle of the present invention is relatively soft and becomes softer while remaining smooth as the patient consumes it. Patients without teeth or with dental work that prevents them from chewing the Nystatin-containing gum are able to suck on a popsicle, which is an ideal way to administer Nystatin and other medications to such patients. The cold and moisture of the popsicle are themselves palliative, even without medication. The flexible container with the popsicle is easy to hold while the popsicle is extruded through the open end of the container. If the patient should happen to fall asleep before the entire popsicle is consumed, unlike the pastille or the gum, the likelihood that the patient could choke is virtually non-existent.

In addition to Nystatin, other local and systemic agents can be administered in frozen form in the drug delivery system of the present invention. For example, antibiotics, analgesics, antipyretics, and other anti-fungal agents could be incorporated into this drug delivery system. Local anesthetics could also be incorporated into the dosage system, either alone or in combination with other medications. These agents would enhance the pain relief produced by the cold of the popsicle.

The Nystatin or other medication may be suspended in a delivery liquid that includes distilled water which has been flavored, preferably with a fruit flavor such as cherry, grape, lime or orange, sweetened with sugar or a sweetener easily tolerated by diabetics and colored to correspond with the flavor. The flavor should be selected to produce a good taste when the medication and delivery liquid are mixed and frozen. This suspension can be added to the containers as described below, stored until dispensed and frozen prior to administration of the medication.

Commercially available suspensions of Nystatin and other medications, which typically contain suspending agents, sweeteners such as sucrose, alcohol and preservatives can also be incorporated into the drug delivery system of the present invention and administered in frozen form. The flavor of the commercially available suspensions is not always acceptable to children, however. Consequently, a frozen popsicle-type medication made from a mixture of the medication and flavored, sweetened and colored water is likely to be better accepted by children.

The dosage of Nystatin that can be administered in the frozen form of the present invention is about 200,000 to 400,000 units. This amount could be administered in frozen form up to 16 times per day, although 4 times per day is a typical administration schedule. The amount of Nystatin or other medication can be varied as required, however, and each frozen dosage unit can contain the quantity of Nystatin deemed optimum for patients of different ages.

Other medications suitable for administration by the system and method of the present invention, such as, for example, Cefaclor, are similarly available in powdered form so that the optimum amount of the medication can be readily determined and included in each frozen dosage unit.

The medication administration system of the present invention can assume a variety of different forms. The system includes a unit of use container that can be frozen to produce a popsicle containing the medication. One type of container that is especially suitable for use in this medication administration system is a flexible plastic tube of the type shown in FIG. 1. This container is substantially cylindrical in shape when filled with liquid and the liquid contents are frozen and is easy to hold by children and the elderly. There are no sharp or rough edges, and the frozen medication-containing mixture is easily extruded from the container simply by pressing on the frozen tube from the unopened end as shown in FIG. 2.

Figure 2:
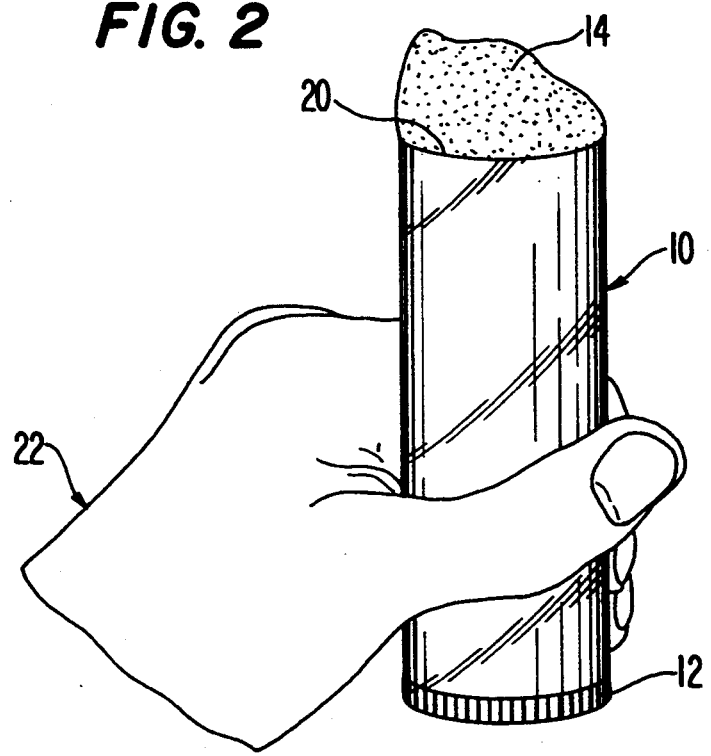
FIG. 2 is a perspective view of the oral medication delivery system according to the present invention in the hand of a patient.

Referring specifically to the drawings, FIG. 1 illustrates a bag or pouch-type container 10 which is preferably formed of a flexible plastic material. This type of container is often formed from a length of substantially cylindrical tubular material that appears flat when it is empty. One end 12 is sealed, typically by a heat sealing treatment suitable for the type of plastic forming the container. A desired quantity of a medication-containing liquid 14 is added to the container, and the opposite end 16 is sealed by heat or another suitable method. A suitably sized air space 18 is left between the top of the liquid 14 and the sealed end 16 to accommodate the expansion of the liquid 14 as it freezes.

The sealed, medication-containing liquid-filled container 10 can be stored in this condition prior to dispensing by a distributor, by a pharmacist or by the patient for whom the medication is prescribed. The container 10 may then be placed in a freezer until the medication-containing liquid 14 is frozen solid. The container may be opened by cutting off end 16, such as along line 20 to form an upper edge of the container. Alternatively, the end 16 could include a tear strip or the like (not shown) which would allow the end of the container to be opened without cutting it. After the container has been opened, it may be held in the hand 22 as shown in FIG. 2 and sucked like a popsicle. The frozen medication-containing liquid 14 can be pushed toward the upper edge 20 of the container by pressure exerted by the hands and fingers.

The material forming the container is preferably a flexible plastic such as polyvinyl chloride or a polyolefin. Polypropylene and polyethylene are particularly suitable. The flexible plastic selected should be inert toward the medication contained in the liquid to be stored and dispensed from the container. The polyolefin plastics are preferred if the liquid medication is to be stored for any period of time. The plastic forming the container may be clear or opaque. Opaque plastic should be used for drugs that are sensitive to light.

The container material and formulation for the liquid contents should preferably be selected to have about the same storage stability as the medication would have in glass, which is about two years.

The container can be formed to have any volume desired. A convenient size container holds from about 30 to 60 ml of medication-containing liquid. This volume accommodates a standard Nystatin dosage of 200,000 to 400,000 units of Nystatin per popsicle. A standard dosage of a commercially available suspension of Nystatin or another kind of medication can also be accommodated by this volume. Nystatin powder, which is used in the other embodiments of the present invention, generally contains about 2,000 units per milligram.

FIG. 3 illustrates a second embodiment of the oral medication delivery system of the present invention. The FIG. 3 embodiment is a flexible plastic substantially cylindrical tube-shaped container 30. Like the FIG. 1 embodiment, the ends 32 and 34 of the container 30 are sealed, preferably by a heat sealing process. The container 30 is separated by a rupturable membrane 36 into two chambers or compartments 38 and 40. Chamber 38 is significantly larger than chamber 40 and occupies most of the volume of the container. However, depending upon the desired solid medication to liquid ratio, the chambers could be substantially equal in volume. Chamber 38 is filled with a delivery liquid 42, which is preferably sweetened flavored distilled water or the like, and chamber 40 contains, in powder form, medication 44 to be mixed with the liquid.

The membrane 36 separating the chambers 38 and 40 is a rupturable membrane formed of an inert material that is capable of forming a barrier between the medication and the liquid when the container is stored. The membrane 36 should rupture in response to pressure so that the powder and liquid can be mixed. The membrane is ruptured by squeezing the container 30 near the end 32 so that the liquid in chamber 38 exerts sufficient pressure on the membrane 36 to rupture it. The membrane 36 may also be formed of a more rigid material that will rupture when the container 30 is twisted. When the membrane is ruptured, the powder 44 is no longer separated from the delivery liquid and can be mixed with the liquid by shaking the container 30. After the medication is suspended in the delivery liquid, the container and liquid contents are frozen.

Chamber 38 should not be filled more than to the liquid fill line 46 to avoid freezing the ruptured membrane with the medication-containing liquid. After the liquid is frozen, the container is cut open at or below the rupturable membrane 36 so that the membrane pieces are removed and will not bother the patient consuming the frozen medication.

The FIG. 3 embodiment is particularly suitable for storing and dispensing medications like Cefaclor which do not have a long shelf life in liquid suspension. The pharmacist or the patient could rupture the membrane and mix the chamber contents prior to freezing. The medication-containing "popsicle" is held and consumed in the same manner as the FIG. 1 embodiment shown in FIG. 2.

FIGS. 4 and 5 illustrate a third embodiment of an oral medication delivery system according to the present invention. This embodiment is similar to that shown in FIG. 3 in that the container 50 is divided by a rupturable barrier or membrane 52 into two chambers 54 and 56. Chamber 54, which is positioned below chamber 56, holds the medication 58 in solid, preferably powdered, form. Chamber 56 holds the sweetened flavored delivery liquid 60 to be mixed with the powdered medication. Positioned in the lower end 62 of the container 50 is a plunger structure 64, which includes a handle 66 and a substantially flat disc-shaped member 68. The disc-shaped member 68 fits in the end 62 of the container 50 tightly and securely to seal this end of the container. An exterior sealing element, such as a suitably configured piece of plastic or foil (not shown) could also be applied to this end of the container to insure a proper seal. The opposite end 70 of the container is sealed with a removable sealing element 72 that will keep the liquid 60 from leaking from the container. A tab 74 may be provided to facilitate the removal of the sealing element 72 at the appropriate time, if the type of sealing element shown is used. Other types of removable sealing elements, for example a plastic cap, could also be used, provided the element forms a leak proof seal with the container upper edge 70.

In the FIGS. 4 and 5 embodiment, the medication 58 and delivery liquid 60 are mixed by exerting sufficient pressure on the handle 66 to move the disc-shaped member 68 and the powdered medication 58 through the rupturable membrane 52. The medication 58 and delivery liquid 60 can then be thoroughly mixed and frozen. FIG. 5 illustrates the ruptured membrane 52, which remains below the disc 68 when the container contents are mixed. This avoids completely the possibility that pieces of the ruptured membrane will be frozen with the medication.

After the medication-containing contents of chamber 56 are frozen hard and ready to be administered to a patient, the sealing element 72 is removed from the top of the container, and the frozen medication is extruded beyond the top edge 70 of the container to allow the patient to suck on it by moving the handle 66 so that the disc 68 pushes the frozen medication toward edge 70.

The container 50 of the embodiment of the oral medication delivery system of FIGS. 4 and 5 is preferably made of a more rigid plastic than the container 30 of FIG. 3 or the container 10 of FIGS. 1 and 2. A more rigid plastic is required to accommodate the plunger arrangement of the disc 68 and handle 66. As this plunger extrudes the frozen medication while it is being consumed by the patient, the handle 66 functions like a "popsicle" stick and provides a convenient handle for the patient to hold without getting his or her hands wet or cold.

Unlike the ice chips that are often used in the treatment of painful oral conditions like candidiasis, the frozen medication of the present invention is very smooth and does not have any rough edges to irritate further the patient's oral lesions. The present oral medication delivery system is also very easy for children and the elderly to hold while the appropriate dose is being consumed. Because popsicles and frozen confections are so readily accepted by children, the oral medication delivery system of the present invention is an ideal way to deliver medications which children typically reject.

The oral medication delivery system of the present invention is particularly well suited for treating oral candidiasis. An effective antifungal agent, preferably Nystatin, but also Ketoconazole, Miconazole or Griseofulvin, can be applied to contact the lesions directly as the frozen popsicle is consumed. In addition, the pain and mouth dryness characteristic of candidiasis are alleviated by the cold and melting popsicle. Anesthetic agents could also be incorporated into the frozen medication mixture to provide additional pain relief.

The amount of the pharmaceutically active substance incorporated into each popsicle may be selected so that the total daily dosage is spread throughout the day, which would require the patient to consume several popsicles. Alternatively, a single dosage popsicle could be formulated which contains the entire amount of medication to be administered. Moreover, the present system can be employed to administer, in frozen form, both medications having a local effect, such as Nystatin for oral candidiasis lesions, and medications having a systemic effect, such as Cefaclor, ibuprofen and acetaminophen for bacterial infections, pain and fever.

INDUSTRIAL APPLICABILITY

The oral medication administration and delivery system and method of the present invention will find their primary applicability in the administration of local and systemic pharmaceutically active agents in frozen form to children, the elderly and others who experience difficulty tolerating such medications when given by available traditional methods of administration.

We claim:

1. An oral medication delivery system for administering at least one local oral or systemic pharmaceutically active agent selected from the group consisting of antibiotic, analgesic, antipyretic, anesthetic and antifungal agents to a patient in a frozen form, wherein said system includes
   (a) sealable container means including a removable seal for holding and storing a desired dose of the pharmaceutically active agent in a stable condition until needed;
   (b) a selected pharmaceutically active agent that is capable of being frozen; and
   (c) a delivery liquid miscible with said pharmaceutically active agent to form a freezable liquid, wherein said delivery liquid is sweetened, flavored and colored to produce a mixture of said active agent and said delivery liquid that is palatable and pleasing to the taste, and wherein a mixture of said pharmaceutically active agent and said delivery liquid is sealed inside said container means and frozen and said seal is removed from said container means so that said frozen mixture may be extruded from said container means.

2. The oral medication delivery system described in claim 1, wherein said container means comprises a substantially cylindrical flexible sealable container formed of a substantially inert material capable of tolerating freezing.

3. An oral medication delivery system for administering at least one local oral or systemic pharmaceutically active agent selected from the group consisting of antibiotic, analgesic, antipyretic, anesthetic and antifungal agents to a patient in a frozen form, wherein said system includes
   (a) sealable container means including a removal seal for holding and storing a desired dine of the pharmaceutically active agent in a stable condition until needed, wherein said container means comprises a substantially cylindrical flexible sealable container formed of a substantially inert material capable of tolerating freezing;
   (b) a selected pharmaceutically active agent that is capable of being frozen; and
   (c) a delivery liquid miscible with said pharmaceutically active agent to form a freezable liquid, wherein said delivery liquid is sweetened, flavored and colored to produce a mixture of said active agent and said delivery liquid that is palatable and pleasing to the taste, and wherein a mixture of said pharmaceutically active agent and said delivery liquid is sealed inside said container means and frozen and said seal is removed from said container means so that said frozen mixture may be extruded from said container means.

4. The oral medication delivery system described in claim 2, wherein said container means is divided into two chambers by rupturable membrane means for forming a removable barrier between the two chambers, said pharmaceutically active agent is in the form of a powder and is disposed within one of said two chambers, said delivery liquid is disposed within the other said chambers, and said rupturable membrane is ruptured by the application of pressure to said delivery liquid so that said delivery liquid can contact said pharmaceutically active agent and be intermixed therewith prior to freezing said container means.

5. The oral medication delivery system described in claim 3, wherein said container means comprises a rigid substantially cylindrical tube formed of a material capable of tolerating freezing and said container means includes rupturable membrane means for separating said container means into first and second chambers, wherein said pharmaceutically active agent in powder form is disposed within said first chamber and said delivery liquid is disposed within said second chamber, removable seal means for sealing said delivery liquid in said second chamber; and plunger means for sealing said pharmaceutically active agent in said first chamber and for rupturing said rupturable membrane to mix said pharmaceutically active agent and said delivery liquid.

6. The oral medication delivery system described in claim 2, wherein said container means is formed from a flexible plastic selected from the group consisting of polyvinyl chloride, polyethylene and polypropylene.

7. The oral medication delivery system described in claim 1, wherein said delivery liquid comprises distilled water, a sweetener, a flavoring agent and a coloring agent.

8. The oral medication delivery system described in claim 7, wherein said sweetener is selected from the group consisting of sugar-containing sweeteners and non-sugar-containing sweeteners.

9. The oral medication delivery system described in claim 1, wherein said container means is sized to hold about 30 to 60 milliliters of said delivery liquid.

10. The oral medication delivery system described in claim 2, wherein the material forming said container means is a flexible plastic selected from the group consisting of clear flexible plastics and opaque flexible plastics.

11. The oral medication delivery system described in claim 5, wherein said substantially cylindrical tube is formed from a rigid plastic selected from the group consisting of clear rigid plastics and opaque rigid plastics.

12. The oral medication delivery system described in claim 1, wherein said pharmaceutically active agent is Nystatin.

13. The oral medication delivery system described in claim 3, wherein said pharmaceutically active agent is Nystatin.

14. The oral medication delivery system described in claim 4, wherein said pharmaceutically active agent is Nystatin.

15. The oral medication delivery system described in claim 5, wherein said pharmaceutically active agent is Nystatin.

16. The oral medication delivery system described in claim 12, wherein 200,000 to 400,000 units of Nystatin is mixed with said delivery liquid.

17. The oral medication delivery system described in claim 5, wherein said plunger means includes sealing element means for sealing said pharmaceutically active agent in said first chamber and handle means attached to said sealing element means for moving said sealing element means and said pharmaceutically active agent into said first chamber to mix with said delivery liquid.

18. A method for delivering and administering oral medication in frozen form to a patient suffering from a local oral or systemic condition requiring treatment, wherein said method includes the steps of:

(a) providing a removably sealed container containing at least one oral local or systemic pharmaceutically active agent selected from the group consisting of antibiotic, analgesic, antipyretic, anesthetic, and antifungal agents in a freezable delivery liquid;

(b) storing said removably sealed container at ambient temperatures until the pharmaceutically active agent is to be administered;

(c) thoroughly mixing said pharmaceutically active agent throughout said delivery liquid;

(d) subjecting the container with the thoroughly mixed contents to a temperature low enough to cause the pharmaceutically active agent mixed in the delivery liquid to freeze to a solid form;

(e) unsealing the container and extruding the solid frozen pharmaceutically active agent and delivery liquid mixture above the unsealed edge of the container; and (f) administering the frozen mixture to said patient.

19. The method described in claim 18, wherein said condition is oral candidiasis and said pharmaceutically active agent is Nystatin.

* * * * *